United States Patent
Boschi et al.

(10) Patent No.: US 8,834,790 B2
(45) Date of Patent: *Sep. 16, 2014

(54) APPARATUS AND METHOD FOR STERILIZING CONTAINER CLOSURES

(75) Inventors: Emanuela Boschi, Parma (IT); Angelo Silvestri, Parma (IT)

(73) Assignee: Sidel S.p.A., Parma (IT)

(*) Notice: Subject to any disclaimer, the term of this patent is extended or adjusted under 35 U.S.C. 154(b) by 429 days.

This patent is subject to a terminal disclaimer.

(21) Appl. No.: 13/060,868

(22) PCT Filed: Aug. 26, 2008

(86) PCT No.: PCT/IT2008/000557
§ 371 (c)(1),
(2), (4) Date: Feb. 25, 2011

(87) PCT Pub. No.: WO2010/023696
PCT Pub. Date: Mar. 4, 2010

(65) Prior Publication Data
US 2011/0158846 A1    Jun. 30, 2011

(51) Int. Cl.
*A61L 2/00* (2006.01)
*A61L 2/18* (2006.01)
*A61L 9/00* (2006.01)
*B67B 3/00* (2006.01)
*B67B 1/03* (2006.01)
*A61L 2/20* (2006.01)

(52) U.S. Cl.
CPC ............... *B67B 1/03* (2013.01); *A61L 2202/23* (2013.01); *B67B 3/003* (2013.01); *A61L 2/208* (2013.01)
USPC ........................................... 422/28; 422/292

(58) Field of Classification Search
CPC ......................................................... A61L 2/20
USPC ........................... 422/28, 292, 300, 302, 304
See application file for complete search history.

(56) References Cited

U.S. PATENT DOCUMENTS

| | | | |
|---|---|---|---|
| 4,981,649 A | | 1/1991 | Shibauchi et al. |
| 4,992,247 A | * | 2/1991 | Foti .............................. 422/304 |
| 5,076,039 A | | 12/1991 | Shibauchi et al. |
| 5,476,634 A | * | 12/1995 | Bridges et al. ................. 422/22 |
| 5,487,873 A | * | 1/1996 | Bridges et al. ............... 588/249 |
| 5,523,052 A | * | 6/1996 | Bridges et al. ................. 422/22 |

(Continued)

FOREIGN PATENT DOCUMENTS

DE    198 51 654 A1    5/2000
EP    0 334 216 B1    7/1993

(Continued)

OTHER PUBLICATIONS

English translation of WO 2000/027440, May 18, 2000.*

*Primary Examiner* — Regina M Yoo
(74) *Attorney, Agent, or Firm* — Pearne & Gordon LLP (57) ABSTRACT

An apparatus (1) for sterilizing container closures comprises a conduit (2) defining a passage for the closure and having a wall (3) surrounding the passage, spraying means (4) for injecting inside the conduit (2) a sterilization fluid heated and vaporized, drying means for introducing hot air in the conduit (2) and means for capturing the exhaust fluids exiting from the con-duit (2), said means comprising at least a suction hood (15) arranged over a corresponding exhaust opening (14) defined in the conduit (2) at a predetermined distance thereto, to capture the exhaust fluids from said exhaust opening (14) bay way of a draught effect.

15 Claims, 6 Drawing Sheets

(56) References Cited

U.S. PATENT DOCUMENTS 5,720,148 A 2/1998 Bedin et al.
5,964,043 A * 10/1999 Oughton et al. ............ 34/92
6,120,730 A * 9/2000 Palaniappan et al. ......... 422/28

FOREIGN PATENT DOCUMENTS

| JP | 2001-240023 | A2 | 9/2001 |
| WO | 00/21838 | A1 | 4/2000 |
| WO | 2006/128884 | A2 | 12/2006 |

* cited by examiner

APPARATUS AND METHOD FOR STERILIZING CONTAINER CLOSURES

TECHNICAL FIELD AND BACKGROUND ART

The present invention relates to an apparatus and a method for sterilizing container closures.

As generally known, in the food industry and in particular in the field of aseptic filling of containers with beverages and in the field of aseptic food packaging, there exists a need to sterilise the containers both internally and externally before they are filled.

Sterilisation is generally achieved using chemical agents, e.g. hydrogen peroxide, which can be used on surfaces of every type, such as paper, plastic, metal or organic materials.

To ensure that filling takes place in aseptic conditions it is necessary to sterilise not only the containers but also their closures, for example caps or stoppers, which serve to seal the containers at the end of the filling process.

In this light, known apparatuses for sterilizing container closures comprise a conduit having a wall defining internally a passage for the closures.

Hence, said known apparatus defines inside the conduit a closed volume having a controlled aseptic atmosphere. Said known apparatus comprises spraying means for injecting inside the conduit a sterilization fluid (i.e. a chemical agent) heated and vaporized, and drying means for introducing hot air in the conduit. The drying means have the function of eliminating the sterilization fluid condensed on the closures, before the closures themselves exit the apparatus. It is noteworthy to observe that the sterilization fluids which are commonly used in these apparatuses are chemically active when their temperature is above a threshold value (activation value).

For this reason, the sterilization fluid is heated before it is injected in vaporized fashion inside the conduit. In this light, the apparatus comprises a device for heating and vaporising the sterilization fluid, for instance as described in patent application WO2006128884 of the same applicant.

A further problem arises in relation to the need of getting rid of the exhaust fluids which exit from the conduit. In fact, the exhaust fluids exiting from the conduit would flow into the environment surrounding the conduit, if the exhaust fluids were not captured.

In this light, it is noteworthy to observe that the standards fix the threshold values (which must not be exceeded) for the concentration of the exhaust fluids in the environment of the sterilization conduit (in fact, said environment is itself kept aseptic).

Therefore, the sterilization apparatus comprises a system for the extraction of the exhaust fluids, from the conduit, in such a way that they do not flow in the environment.

In the known apparatus, an exhaust tube is provided, which is connected to a suction pump at one end and directly to the conduit at the opposite end. In this way, a suction force is directly applied to the volume inside the conduit.

In this light, a problem arises is relation to the extraction of the exhaust fluids from the conduit.

In fact, said extraction of exhaust fluids generates undesired flows of the process fluids (i.e. the sterilization fluid and the drying air) inside the conduit, thus altering the distribution of the process fluids themselves.

Therefore, the distribution of the process fluids inside the conduit is not optimized because it is affected by the suction force applied by the system for extracting the exhaust fluids.

In addition, the action of the process fluids on the closures is hardly controllable and predictable, due to the fact that the distribution of the process fluids inside the conduit is affected by the extraction of the exhaust fluids.

A further problem arises is relation to the need to activate the sterilization fluid. In fact, because the whole volume inside the conduit must be aseptic, the need arises of securing that the whole amount of fluid present inside the conduit be at a temperature above the activation value.

Thus, it is desirable that also the sterilization fluid that is condensed on the internal surface of the wall of the conduit be active (i.e. above the activation threshold).

For this purpose, in the operation of the sterilization process, the enthalpy of the process fluids (i.e. the sterilization fluid and the drying air) is regulated taking account of the fact that a portion of said enthalpy is needed to heat the conduit wall.

Therefore, in the known apparatus the process fluids (i.e. the sterilization fluid and the drying air), which are oriented towards the closures in order to treat them as described above, heat the fluid filling the volume internal to the conduit 2, and thus indirectly heat the conduit wall 3.

However, this known apparatus has the following drawbacks.

First of all, in the known apparatus the process fluids are not optimized for the treatment (i.e. sterilization) of the closures; in fact, the use of a portion of the enthalpy of the process fluids to obtain the heating of the conduit wall is a waste of energy.

In addition, a use of process fluids which is excessive with regard to the sterilization purposes (excessive with regard to either the flow rate or the temperature of the process fluids themselves) determines a risk of damaging the closures; in fact, en excessive heat is transferred to the closures; in particular, the temperature of the process fluids is too high.

A further prior art is known from document WO 00/21838 disclosing an apparatus for sterilising lids for food packaging.

According to another prior art, document U.S. Pat. No. 5,720,148 discloses a device for filling bottles, especially plastic bottles, with a liquid, wherein said device includes an air separation liquid station, a flash pasteurization station, a station for saturating the liquid with a sterile inert gas with respect to the liquid, a bottle washing station and stoppers with a liquid disinfectant with under hood drying in a treated atmosphere, a bottle filling station, preferably by means of gravity filling under a slight partial vacuum, a station for degassing the inert gas, and a stoppering station.

A further prior art is known from document EP 334216 disclosing methods and means for lid sterilization and temporal sealing.

Document DE 19851654 shows a method and a device for sterilising screwcaps which are treated with atomised hydrogen peroxide, then dried and conveyed to a sanitation chamber for further treatment.

DISCLOSURE OF THE INVENTION

An object of the present invention is to eliminate the aforesaid drawbacks and to make available an apparatus and a method for sterilizing container closures, which provides a capturing of exhaust fluids exiting form the conduit without affecting the distribution of the process fluids inside the conduit.

An additional object is to make available an apparatus and a method for optimizing the parameters which regulate the extraction of the exhaust fluids form the conduit, in order to minimize the perturbation of the process fluids inside the conduit.

Said objects are fully achieved by the apparatus of the present invention, which is characterised by the content of the claims set out below.

BRIEF DESCRIPTION OF THE DRAWINGS

These and other features shall become more readily apparent from the following description of a preferred embodiment, illustrated purely by way of non limiting example in the accompanying drawing tables, in which.

BEST MODE FOR CARRYING OUT THE INVENTION

With reference to the Figures, the numeral 1 globally designates an apparatus for sterilizing container closures, such as caps or stoppers, which serve to seal the containers and are applied to the containers at the end of the filling process. The apparatus 1 comprises a conduit 2 defining a passage for the closures. The conduit 2 has at least one wall 3; in particular, the conduit 2 has a lateral wall 3 which surrounds the passage for the closures.

The conduit 2 has, in the illustrated example, a rectangular section; accordingly, the wall 3 comprises four faces, each having substantially flat shape.

In addition, the conduit 2 is preferably arranged along a longitudinal direction. However, such a configuration of the conduit 2 is not essential; in fact, the conduit 2 may have a different shape, for example a tube having a wall 3 with circular section and arranged on a curved path.

Inside the conduit 2 a conveyor is arranged (not shown in the figures) to transport the closures form an inlet to an outlet of the conduit 2 itself. Said inlet and outlet correspond to the inlet and outlet of the apparatus 1. The apparatus 1 receives (singularly) at the inlet the closures to be sterilized and makes available the same closures at the outlet after their sterilization.

The closures inside the conduit 2 are preferably arranged with their bottom wall face up and their concave portion face down.

The apparatus 1 also comprises a plurality of nozzles 4 coupled to the conduit 2 for injecting a sterilization fluid inside the conduit 2.

The apparatus is also provided with a system for heating and/or vaporizing the sterilization fluid, in order to feed the nozzles 4 with sterilization fluid which is heated above the activation temperature for that fluid and is vaporized. Such a system, not shown in the figures, is described in patent application WO2006128884 of the same applicator, which is here incorporated by reference.

Therefore, the nozzles 4, together with said system (i.e. the system for heating and vaporizing the sterilization fluid), define spraying means for injecting inside the conduit 2 a sterilization fluid heated and vaporized.

Said sterilization fluid is preferably Vapour of Hydrogen Peroxide (VHP).

In particular, the spraying means comprises a first delivery pipe 5, which is arranged inside the conduit 2. The first delivery pipe 5 is provided with a plurality of holes along its length, which define the nozzles 4. The first delivery pipe 5 is fed with the sterilization fluid (heated and vaporized as described above) at one of its ends and is closed at an opposite end (said closed end is indicated with the reference number 6 in the figures).

Furthermore, the apparatus 1 comprises drying means for introducing hot air in the conduit, for the purpose of removing the sterilization fluid condensed on the closures.

In the preferred embodiment illustrated in the figures, the drying means comprises a second delivery pipe 7, which has a structure similar to that of the first delivery pipe 5 (i.e. is arranged inside the conduit 2 and has a closed end) but is fed with heated air (or any inert gas).

Therefore, the drying means is configured to provide a flow of hot air able to intercept the closures passing inside the conduit 2. Said air tubes are connected to a source of heated air, and aseptic filters are inserted downstream the source of heated air, to secure that the environment inside the conduit 2 is kept aseptic. The drying means are coupled to the conduit 2 substantially downstream with respect to the spraying means, in the direction of movement of the closures inside the conduit 2.

In this light, it is important to observe that the conduit 2 preferably defines three operative portions, which are arranged consecutively along the path followed by the closures in their movement inside the conduit 2.

A first operative portion is provided with the first delivery pipe 5 (and thus with the nozzles 4), i.e. it is the portion where the spraying means is active.

A third operative portion is provided with the second delivery pipe 7, i.e. it is the portion where the drying means is active.

A second operative portion, intermediate between the first and the second operative portion, is a portion where neither the spraying means nor the drying means is directly active on the closures (i.e. neither the first delivery pipe 5 nor the second delivery pipe 7 is arranged in the second operative portion of the conduit 2).

In addition, the apparatus 1 originally comprises means for heating the wall of the conduit, operatively coupled thereto.

Said means for heating the wall 3 are preferably coupled to at least one of the faces of the wall 3 of the conduit 2 on its whole length, i.e. along the path followed by the closures in their movement inside the conduit 2. Hence, means for heating the wall 3 are coupled to at least one face of the wall 3 of all of the three operative portions of the conduit 2 described above.

This feature has the advantage that length of the second operative portion of the conduit 2 may be set to a desired value (said length having an influence on the overall performance of the apparatus 1 and thus being a parameter to be optimized) and the flow of the process fluids (i.e. sterilizing fluid and drying air) set independently at a desired optimized value, the wall 3 of the conduit 2 (including the second operative portion of the conduit 2) being heated independently with respect to the process fluids.

In the preferred embodiment of the apparatus 1, illustrated in the figures, said means for heating the wall 3 of the conduit 2 comprises a heating layer 8 attached to the external surface of the conduit wall 3. This layer 8 is provided with a plurality of electric resistors.

Thus, the electric resistors are associated to the heating layer 8 attached to said external surface of the wall 3.

In particular, said layer 8 comprises a plurality of stripes having an adhesive surface to be coupled to the faces of the wall 3 of the conduit 2. The electric resistors are associated to said stripes, according to a known technique. Therefore, at least an electrical resistor is directly coupled to an external surface of the wall 3 of the conduit 2, providing a heater of the wall 3 itself directly coupled thereto. The heater (the electric resistors) is connected to an electric power source 9, and transfers directly to the wall 3 of the conduit 2 the heat generated by virtue of Joule effect.

In particular, the apparatus 1 comprises a plurality of electric resistors connected in parallel to the electric power source 9.

It is noteworthy to observe that said power source is independent from said spraying means and drying means (i.e. the sterilization fluid and the drying air have are not used for heating the conduit wall).

The latter feature is particularly important, because it allows to heat the conduit wall 3 without interfering with the sterilization process, which is regulated by the process fluids (i.e. the sterilization fluid and the drying air).

It also has to be noted that the heater is coupled to the conduit 2 in such a way as to maximize the portion of wall 3 where heat is exchanged.

In the preferred embodiment illustrated in the figures, the conduit wall 3 has a transparent portion 10 for inspecting the interior of the conduit 2 (and in particular the Closures conveyed inside the conduit 2).

I this light, said heater (i.e. the layer 8 provided with the electrical resistors) is operatively active on the whole remaining portion of the conduit wall 3.

In is noteworthy to observe that the means for heating the wall 3 of the conduit 2, according to an alternative embodiment not shown in the figures, comprises a duct (or a plurality of ducts) wherein heating fluid is pumped, the duct being is arranged in contact with the conduit wall 3, thus providing a heat exchanger able to increase the temperature of the conduit wall. Said heating fluid may be taken form any heating source (preferably independent from the process fluids) and does not require to be filtered, since it does not come into contact with the aseptic environment internal to the conduit 2.

According to a further aspect of the present invention, the apparatus 1 is provided with a system for controlling the temperature of the conduit wall 3. The aim of this system is to maintain the wall temperature at a desired value avoiding any waste of energy. A further aim of this system is to monitor the means for heating the conduit, detecting possible faults and bad functioning.

In this light, the apparatus 1 comprises at least a sensor 11 (e.g. a thermocouple) coupled to the wall 3 of the conduit 2 to detect the temperature thereof, and an electronic card 12, which constitutes control means connected to the power source 6 and to the sensor 11 to regulate retroactively the power transferred to the heater (and therefore the heat transferred to the wall 3), in such a way that the temperature of the conduit wall 3 has a desired value (i.e. a reference value Tref).

Said desired value is not lower than the activation value of temperature of the chemical agent used as sterilization fluid. For example, said desired value for the temperature of the conduit wall ranges from approximately 50° C. to approximately 130° C., when VHP is used as sterilization fluid.

Preferably, the apparatus 1 comprises a plurality of sensors 11 coupled to different points of the conduit wall 3, to detect corresponding temperature values of the conduit wall. These detection points are preferably longitudinally spaced along the whole length of the conduit wall 3; more preferably, at least a sensor 11 is provided in correspondence to each of the three operative portions of the conduit 2.

In addition, each sensor 11 is preferably coupled to a portion of the wall 3 wherein a corresponding heater is coupled (where a plurality of heaters, each e.g. formed by a plurality of resistors, are arranged in parallel).

This is particularly important in combination with the fact that the means for heating the conduit wall 3 comprises a plurality of heaters connected in parallel and arranged along the conduit aligned longitudinally.

In fact, in this way it is possible to detect if a portion of the conduit wall 3 has a temperature lower than the rest of the conduit wall (and maybe lower than the activation value). This may be caused by a fault of one of the heaters (e.g. one of the panels constituting the layer 8 of electric resistors).

In this case, the control means are configured to regulate the power transferred to the other heaters (the ones which are working properly) to maintain the desired temperature of the conduit wall 3 (thus maintaining the wall 3 at a uniform and constant temperature), and at the same time for activating alert means in response to the detected fault condition.

It is noteworthy to observe that the power source 9 preferably comprises a source of continuous voltage (e.g. any alternate power source coupled to a rectifier or any other alternative solution) connected to a converter 13 defining a module for a PWM modulation of a voltage applied to the resistors.

Figure 1:
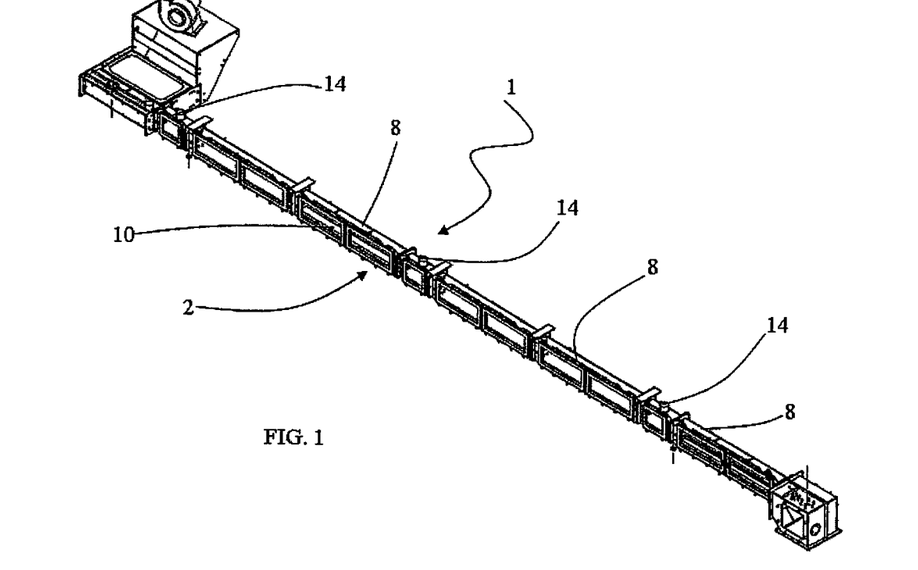
FIG. 1 shows the apparatus according to the present application, in perspective view.
Figure 2:
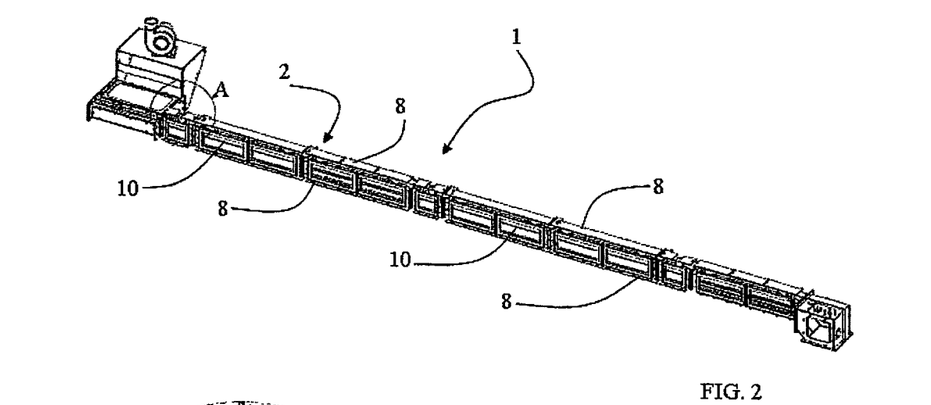
FIG. 2 shows the apparatus of FIG. 1, in a different perspective view.
Figure 3:
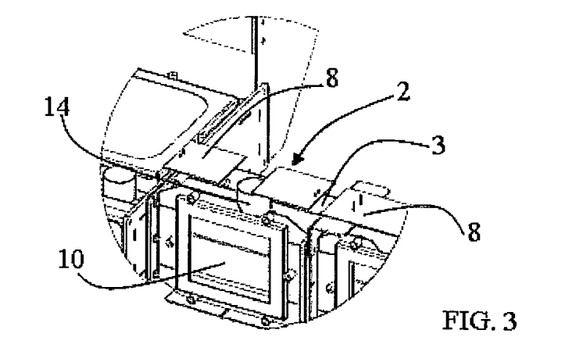
FIG. 3 shows an enlarged view of the portion A of FIG. 2.
Figures 4, 5, 6:
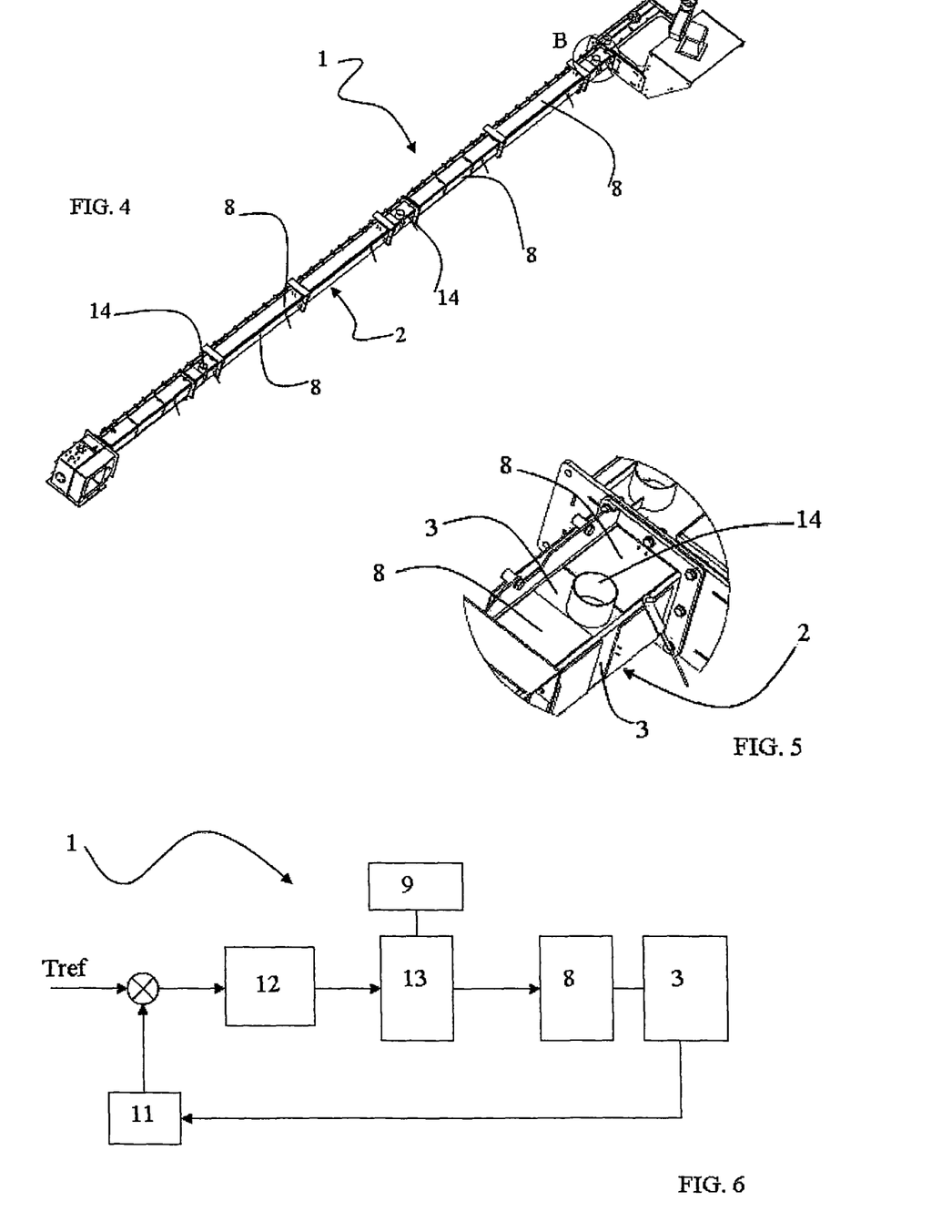
FIG. 4 shows the apparatus of FIG. 1, in a further perspective view.
FIG. 5 shows an enlarged view of the portion B of FIG. 4.
FIG. 6 shows a functional diagram pertaining to the method according to the present patent application.
Figure 7:
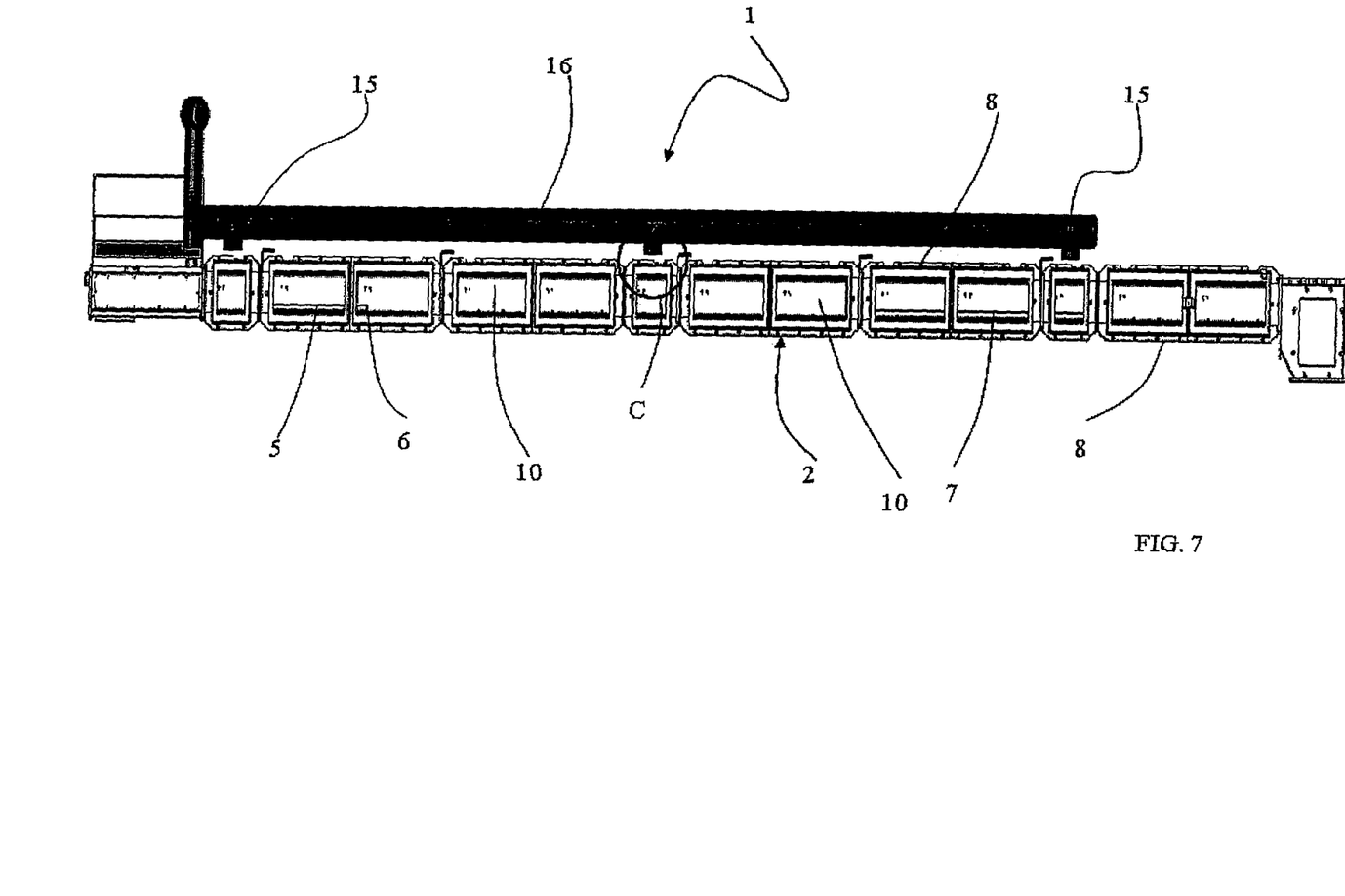
FIG. 7 shows the apparatus according to the present application including the system for the extraction of the exhaust fluids, in lateral view.
Figure 8:
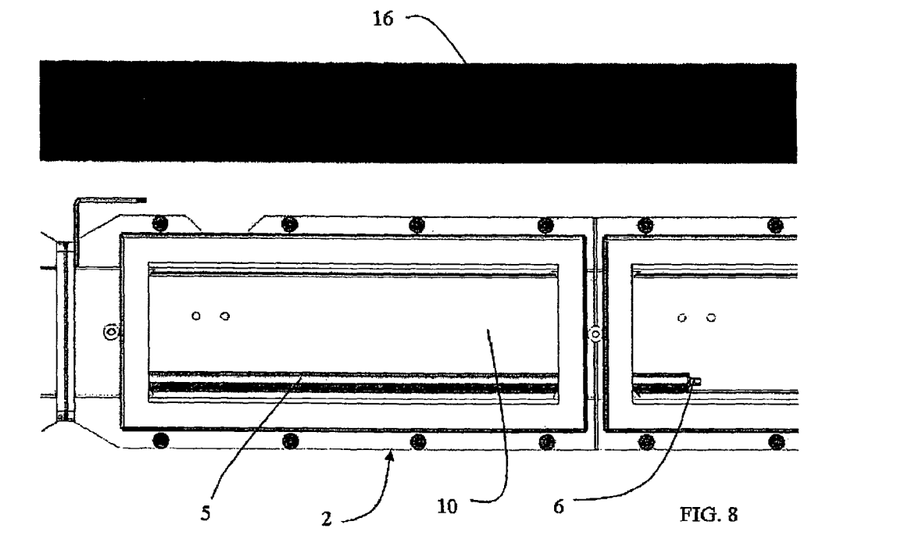
FIG. 8 shows an enlarged view of a first operative portion of the apparatus of FIG. 7.
Figure 9:
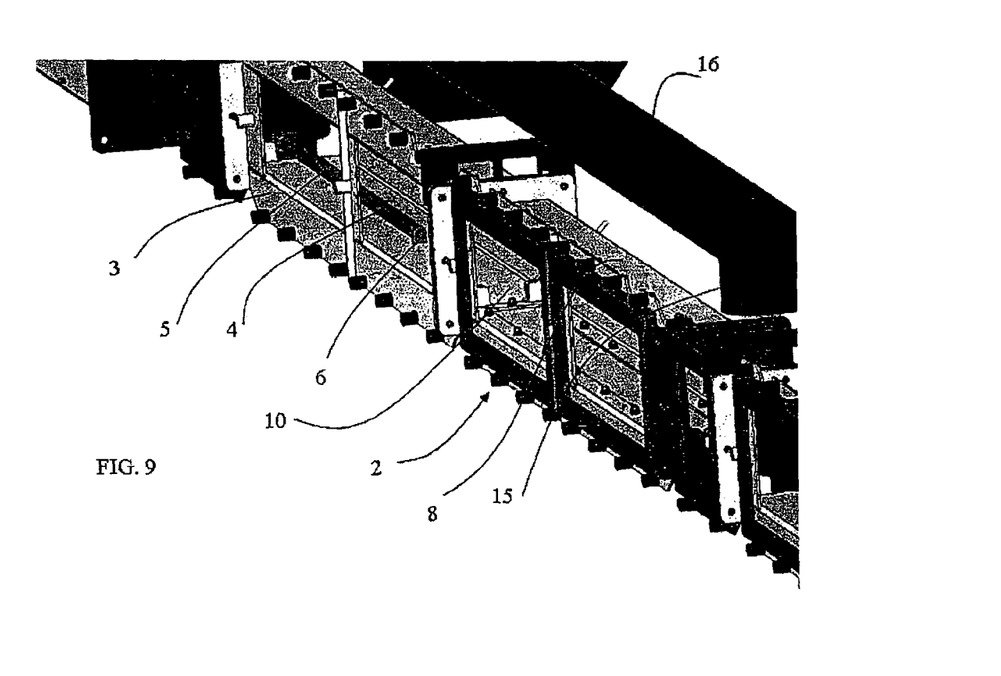
FIG. 9 shows the portion of FIG. 8, in a perspective view.
Figure 10:
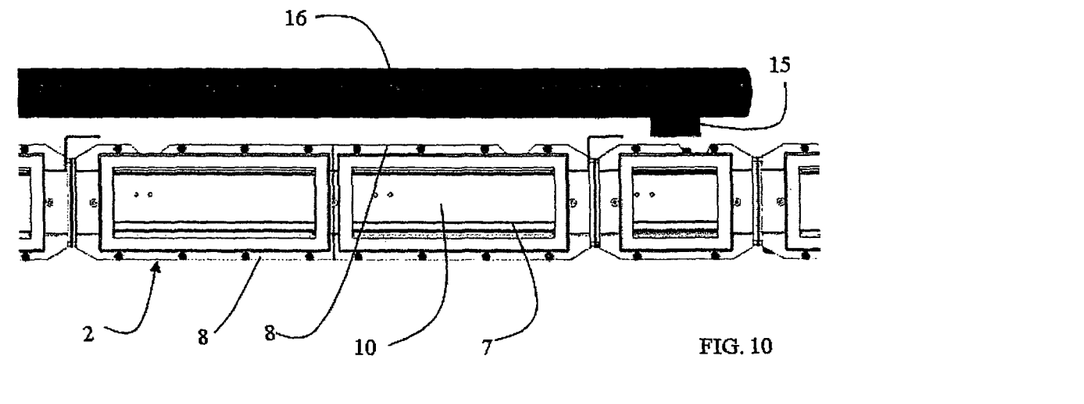
FIG. 10 shows an enlarged view of a third operative portion of the apparatus of FIG. 7.
Figure 11:
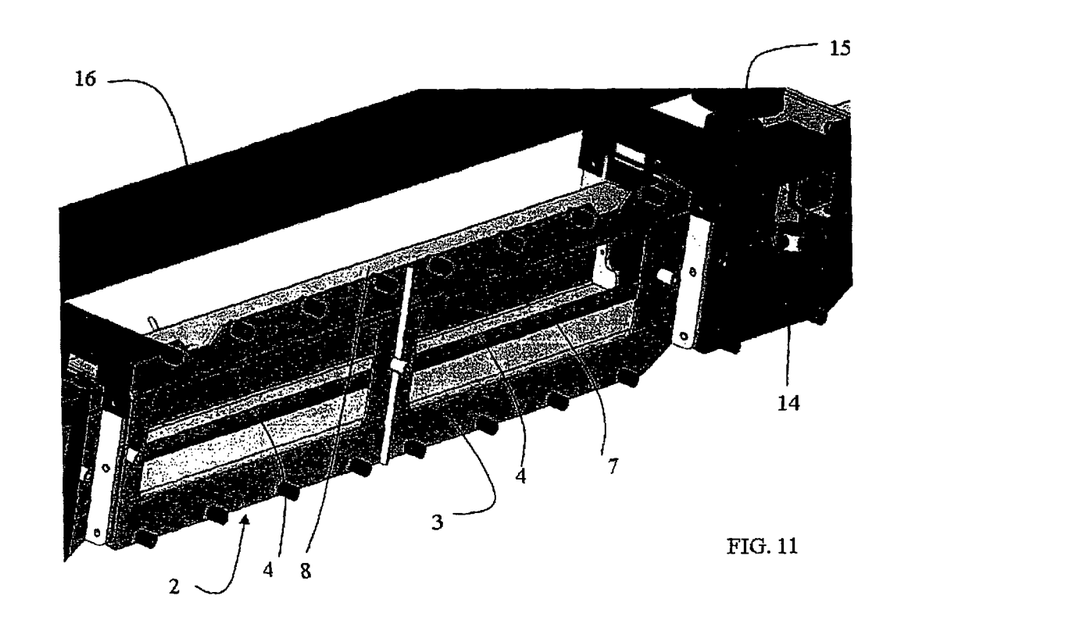
FIG. 11 shows the portion of FIG. 10, in a perspective view.
Figure 12:
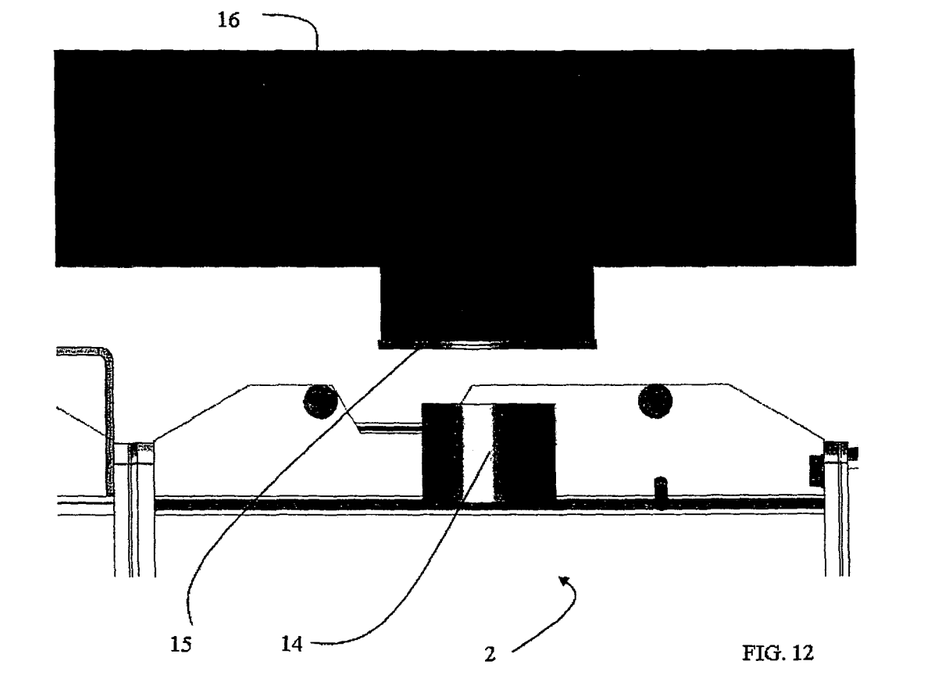
FIG. 12 shows an enlarged view of portion C of FIG. 7.

In this light, the control means 12 are connected to said converter 13 in order to drive it in response to the result of the comparison between the reference temperature value (Tref) and the temperature values detected by the sensors 11 (as schematically shown in FIG. 9).

The apparatus 1 also comprises a system for capturing the exhaust fluids which exit from the conduit 2.

Such a system comprises exhaust connections 14 consisting of outlets defined in the upper portion of the conduit 2 wall 3 and extending upwards.

These exhaust connections 14 cooperate with corresponding suction hoods 15 defined in a exhaust tube 16, wherein a suction pump is preferably inserted. According to an alternative embodiment, the suction pump is substituted with an exhaust tube 16 defining a vertical column in correspondence to the exhaust openings 14, in such a way to provide an adequate natural draught.

It is noteworthy to observe that the upper end of the exhaust connection 14 is arranged at a predetermined distance from the lower end of the correspondent suction hood 15, to provide a capturing of the exhaust fluids exiting form the conduit 2 without extracting the exhaust fluids directly form the conduit, thus without applying a suction force to the inside of the conduit 2.

Preferably, a plurality of exhaust connections 14 and correspondent suction hoods 15 is provided; in the illustrated embodiment three connections 14 and correspondent suction hoods 15 are provided, each suction hood 15 being arranged in correspondence of a respective operative portion of the conduit 2. Preferably, the suction hood 15 has a section which is larger than the section of the correspondent exhaust connection 14.

Such a feature allows to provide a step of capturing the exhaust fluids exiting from the exhaust opening 14 of the conduit 2 and shifting laterally while moving upwards.

In this way, the exhaust fluids present inside the exhaust opening 14 are captured by way of a suction principle analogous to that of a hood draught (e.g. the draught of a hood provided in a professional kitchen to capture the fumes produced by the cooking).

In addition, each suction hood 15 is provided with means for adjusting the effective section of the suction hood 15 itself.

These means for adjusting the effective section of the suction hood 15 (illustrated in FIG. 13) comprises preferably a fist flange 17 and a second flange 18 arranged inside the suction hood 15 in contact with each other and in such a way to be rotated one with respect to the other.

Figure 13:
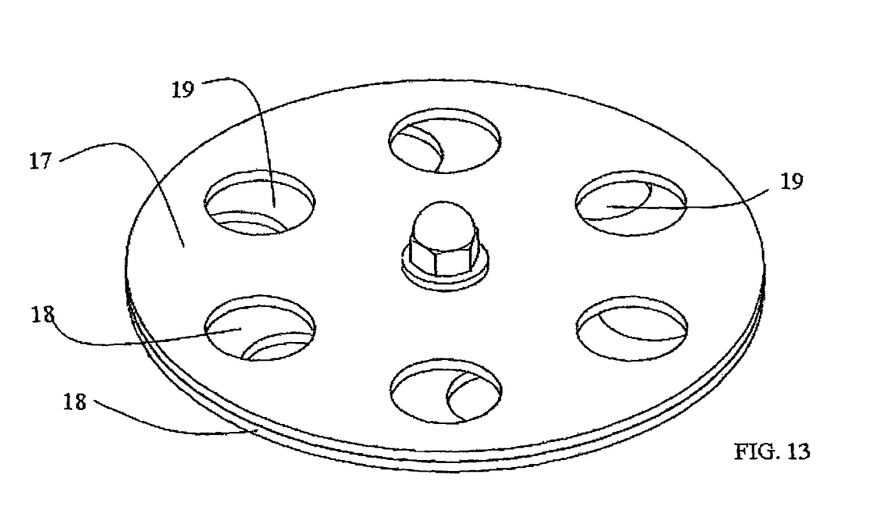
FIG. 13 shows an internal portion of the apparatus of FIG. 7.

Said fist flange 17 and second flange 18 define apertures 19 which increase or decrease their overlap as a function of the reciprocal angular position of the fist flange 17 and second flange 18.

Thus, when the overlap of corresponding apertures 19 of the flanges 17 and 18 is minimum, the effective section of the suction hood 15 is accordingly minimized; likewise, when the overlap of corresponding apertures 19 of the flanges 17 and 18 is maximum, the effective section of the suction hood 15 is accordingly maximized.

Alternatively to or additionally to said means for adjusting the effective section of the suction hood 15, means are provided (not illustrated because itself known) to vary the power applied to the suction pump inserted in the exhaust tube 16, with the possibility to control said means (e.g. the pump may be driven by an electric power source through an inverter controlled by an electronic card).

It is noteworthy to observe that such a distance (between the upper end of the exhaust connection 14 and the lower end of the correspondent suction hood 15), the effective section of the suction hood 15 and the ratio between the section of the upper end of the exhaust connection 14 and the section of the lower end of is the correspondent suction hood 15 (the former section being smaller than the latter section) constitute parameters which are set in order to minimize the effect of the system for extracting exhaust fluids from the conduit 2 on the distribution of the fluids contained inside the conduit.

In such a way, the fluid-dynamic distribution of the process fluid inside the conduit 2 is not affected by the extraction of the exhaust fluids; in fact, the exhaust fluids are captured by way of a draught principle, and no suction force is directly applied to the fluid contained inside the conduit 2.

Such a result improves the performance of the apparatus, because it avoids undesired flows of process fluids inside the conduit 2, and thus it allows to control the distribution of the process fluids inside the conduit 2 optimizing their effect on the closures.

It is further object of the present invention a method for sterilizing container closures transported inside a conduit 2 having a wall 3 defining internally a passage for the closures.
Said method comprises the following steps:
injecting inside the conduit 2 a sterilization fluid heated and vaporized (VHP);
introducing hot air in the conduit for drying the closures,
heating the wall 3 of the conduit 2 by transferring heat directly to the conduit wall.

It is noteworthy to observe that the heating step entails the heating the wall 3 on the whole length of the conduit 2, thus heating all of the three operative portions of the conduit 2.

Preferably, in the heating step, the heat is transferred to the wall 3 from a heat source which is independent from the process fluids (i.e. said sterilization fluid and said drying air).

In particular, the heating step entails the transmission of energy from a power source independent from said spraying means and drying means to at least a heater directly coupled to an external surface of the conduit wall 3.

Preferably, said heater is an electrical resistor (or a layer 8 attachable to the wall 3 and provided with a plurality of resistors connected with each other) and said power source is an electric power source; in this light, the heating step entails the transmission of electrical energy from the electrical power source to said at least a heater.

The method further comprises a step of detecting at least a value of the temperature of the conduit wall 3, and a step of regulating retroactively the power transferred to the heater, in such a way that the temperature of the conduit 2 wall 3 has a desired value (as described above with respect to the apparatus 1). Preferably, the sterilization fluid is VHP and said desired value for the temperature of the conduit wall ranges from approximately 50° C. to approximately 130° C.

Said detection step preferably entails the coupling of a plurality of sensors 11 to different points of the conduit wall 3, to detect corresponding temperature values of the conduit wall. More preferably, the detecting step entails the detection of at least a temperature value in correspondence of each of the three operative portions of the conduit 2.

In addition, preferably the heater is defined by layers 8 comprising electrical resistors and attached to the external surfaces of the conduit 2 wall 3.

In this light, said regulating step entails a PWM modulation of a voltage applied to the resistor.

It is noteworthy to observe that the heating step, according to an alternative embodiment, comprises a step of pumping a heating fluid (i.e. a hot fluid) through a duct (or a plurality of ducts) arranged in contact with the conduit wall 3, thus providing a heat exchange (from the heating fluid to the wall 3) in order to increase the temperature of the wall 3 of the conduit 2.

In fact, the heat transferred in the heating step may be transferred by a conduction principle (heat transferred to the wall 3 e.g. from electric resistors directly coupled to the wall itself) or by convection principle (heat transferred to the wall 3 e.g. from a heating fluid conveyed along a surface, and in particular the external surface, of the wall itself).

The method according to the present application further comprises a step of extracting exhaust fluids from the conduit 2.

Such an extracting step entails a step of arranging a plurality of consisting of outlets defined in the upper portion of the conduit 2 wall 3 and extending upwards (defining exhaust connections 14), cooperating with corresponding suction hoods 15 defined in a exhaust tube 16, wherein a suction pump is inserted (according to the description above of the apparatus 1).

Hence, the extracting step consists of capturing the exhaust fluids by way of a draught principle.

The extracting step further comprises a step of adjusting the effective section of the suction hoods 15.

Such an adjusting step entails preferably the rotation of a fist flange 17 with respect to a second flange 18, these flanges being arranged in contact with each other inside the suction hood 15, in such a way to be rotatable one with respect to the other. Said fist flange 17 and second flange 18 define apertures 19 which increase or decrease their overlap as a function of the reciprocal angular position of the fist flange 17 and second flange 18 (according to the description above of the apparatus 1).

It is noteworthy to observe the upper end of the exhaust connection 14 is arranged at a predetermined distance from the lower end of the correspondent suction hood 15.

Such a distance (between the upper end of the exhaust connection 14 and the lower end of the correspondent suction hood 15), the effective section of the suction hood 15 and the ratio between the section upper end of the exhaust connection 14 and the section of the lower end of the correspondent suction hood 15 (the former section being smaller than the latter section) constitute parameters which are set in order to minimize the effect of the system for extracting exhaust fluids from the conduit 2 on the distribution of the fluid contained inside the conduit.

Hence, the method according to the present application further comprises a step of adjusting these parameters to minimize the effect of the system for extracting exhaust fluids from the conduit 2 on the distribution of the fluid contained inside the conduit 2.

The invention described above provides the following advantages.

The apparatus and method for sterilizing closures according to the present invention allow to maintain the wall 3 of the conduit 2 at a desired temperature value (above the activation value of the sterilization fluid injected in the conduit) independently on the operation of the process fluids (i.e. the sterilization fluid and the drying air injected in the conduit 2).

Therefore, the temperature and the flow rate of the process fluids are optimized is for the sterilization of the closures, thus avoiding waste of energy and any risk of damaging the closures.

In addition, the apparatus and method for sterilizing closures according to the present invention allow an optimization of the energy used to heat the conduit wall and provide a control system able to achieve an automatic regulation and detection (also providing alert signals) of possible faults in the heating of the conduit wall.

The apparatus and method for sterilizing closures according to the present invention further allow to provide a uniform and constant temperature of the conduit wall, thanks to said control system in combination with the presence of a plurality of sensors coupled at different points of the conduit wall for multiple temperature detection.

A further advantage is to improve the performance of the apparatus avoiding undesired flows of process fluids inside the conduit 2, and thus allowing to control the distribution of the process fluids inside the conduit 2 optimizing their action on the closures.

Such a result is possible because, in the step of extracting the exhaust fluids, the exhaust fluids are captured by way of a draught principle (hence no suction force is directly applied to the fluid contained inside the conduit 2), thus allowing the fluid-dynamic distribution of the process fluid inside the conduit 2 not being affected by the extraction of the exhaust fluids.

The invention claimed is:

1. An apparatus for sterilizing container closures, comprising:
   a conduit defining a passage for the container closures and having a wall surrounding the passage;
   spraying means for injecting inside the conduit a sterilization fluid heated and vaporized;
   drying means for introducing hot air in the conduit;
   means for capturing exhaust fluids exiting from the conduit, said means for capturing exhaust fluids comprising at least a suction hood arranged over a corresponding exhaust opening defined in the conduit at a predetermined distance thereto, to capture the exhaust fluids from said exhaust opening by way of a draught effect, whereby no suction force is directly applied to a fluid contained inside the conduit;
   a section of said suction hood being larger than a section of the corresponding exhaust opening.

2. The apparatus according to claim 1, comprising means for adjusting an effective section of the suction hood.

3. The apparatus according to claim 2, wherein said means for adjusting the effective section of the suction hood comprises a first flange and a second flange arranged inside the suction hood in contact with each other and in such a way that they can be rotated one with respect to the other, each flange defining apertures overlapping as a function of the relative rotation of the flanges.

4. The apparatus according to claim 1, wherein the conduit comprises:
   a first operative portion coupled to the spraying means;
   a third operative portion coupled to the drying means;
   a second operative portion intermediate between said first and third operative portions, wherein neither the spraying means nor the drying means is coupled,
   at least three exhaust openings, each one of them being coupled to a respective operative portion of the conduit.

5. The apparatus according to claim 1, comprising means for heating the wall of the conduit operatively coupled thereto.

6. The apparatus according to claim 5, wherein said means for heating the wall of the conduit comprises at least a heater coupled to an external surface of the wall and connected to a power source independent from said spraying means and drying means.

7. The apparatus according to claim 6, wherein said heater is an electric resistor connected to the power source in the form of an electric power source.

8. The apparatus according to claim 5, comprising:
   at least a sensor coupled to the wall of the conduit to detect the temperature thereof;
   control means connected to the means for heating the wall and to the sensor, to regulate retroactively the heat transferred to the wall, in such a way that the temperature of the conduit wall has a desired value.

9. The apparatus according to claim 5, wherein the means for heating the conduit wall is applied to the whole length of the wall of the conduit.

10. An apparatus for sterilizing container closures, comprising:
   a conduit defining a passage for the container closures and having a wall surrounding the passage;
   spraying means for injecting inside the conduit a sterilization fluid heated and vaporized;
   drying means for introducing hot air in the conduit;
   means for capturing exhaust fluids exiting from the conduit, characterized in that said means for capturing exhaust fluids comprises at least a suction hood arranged over a corresponding exhaust opening defined in the conduit at a predetermined distance thereto, to capture the exhaust fluids from said exhaust opening by way of a draught effect, whereby no suction force is directly applied to a fluid contained inside the conduit;
   means for heating the wall of the conduit operatively coupled thereto;

at least one sensor coupled to the wall of the conduit to detect the temperature thereof;

control means connected to the means for heating the wall and to the at least one sensor, to regulate retroactively the heat transferred to the wall, in such a way that the temperature of the wall has a desired value.

11. A method for sterilizing container closures being transported inside a conduit having a wall defining internally a passage for the container closures, comprising the following steps:

injecting inside the conduit a sterilization fluid heated and vaporized;

introducing hot air in the conduit for drying the container closures;

capturing exhaust fluids exiting from the conduit;

providing at least a suction hood arranged over a corresponding exhaust opening defined in the conduit at a predetermined distance thereto, to provide a step of capturing the exhaust fluids from said exhaust opening by way of a draught effect;

wherein a section of the suction hood is larger than a section of the corresponding exhaust opening, to provide a step of capturing the exhaust fluids exiting from the exhaust opening of the conduit and shifting laterally while moving upwards.

12. The method according to claim 11, comprising a step of regulating an effective section of said at least a suction hood, in order to minimize the effect of the capturing step on the distribution of the fluids contained inside the conduit.

13. The method according to claim 12, comprising a step of detecting at least a value of temperature of the wall of the conduit, and a step of regulating retroactively the heat transferred to the wall, in such a way that the temperature of the wall has a desired value.

14. The method according to claim 11, comprising a step of heating the wall of the conduit by transferring heat directly to the wall.

15. The method according to claim 11, comprising a step of regulating an effective section of said suction hood, in order to minimize the effect of the capturing step on the distribution of the exhaust fluids contained inside the conduit.

* * * * *